US012290353B2

(12) United States Patent
Sonkusale et al.

(10) Patent No.: US 12,290,353 B2
(45) Date of Patent: May 6, 2025

(54) THREAD-BASED REAL-TIME MONITORING OF BODILY FLUIDS

(71) Applicant: Trustees of Tufts College, Medford, MA (US)

(72) Inventors: Sameer Sonkusale, Lincoln, MA (US); Trupti Terse, Natick, MA (US)

(73) Assignee: Trustees of Tufts College, Medford, MA (US)

( * ) Notice: Subject to any disclaimer, the term of this patent is extended or adjusted under 35 U.S.C. 154(b) by 793 days.

(21) Appl. No.: 17/276,970

(22) PCT Filed: Sep. 18, 2019

(86) PCT No.: PCT/US2019/051636
§ 371 (c)(1),
(2) Date: Mar. 17, 2021

(87) PCT Pub. No.: WO2020/106353
PCT Pub. Date: May 28, 2020

(65) Prior Publication Data
US 2022/0031204 A1    Feb. 3, 2022

Related U.S. Application Data

(60) Provisional application No. 62/732,627, filed on Sep. 18, 2018.

(51) Int. Cl.
*B01L 3/00*    (2006.01)
*A47L 15/42*    (2006.01)
(Continued)

(52) U.S. Cl.
CPC ........ *A61B 5/14517* (2013.01); *A61B 5/1477* (2013.01); *G06F 1/163* (2013.01)

(58) Field of Classification Search
CPC .............. A61B 5/14517; A61B 5/1477; A61B 5/14532; A61B 5/14546; A61B 5/207; A61B 5/6802; A61B 5/6833; G06F 1/163
See application file for complete search history.

(56) References Cited

U.S. PATENT DOCUMENTS

2004/0158137 A1* 8/2004 Eppstein ............ A61B 5/15134
                                                      600/347
2013/0131563 A1* 5/2013 Ettner .................... A61H 99/00
                                                      601/148
(Continued)

FOREIGN PATENT DOCUMENTS

EP         3385708 A1 * 10/2018
KR     20170041291 A      4/2017
(Continued)

OTHER PUBLICATIONS

Liu, Xiyuan, and Peter B. Lillehoj. "Embroidered electrochemical sensors for biomolecular detection." Lab on a Chip 16.11 (2016):2093-2098. (Year: 2016).*
(Continued)

*Primary Examiner* — Jennifer Wecker
*Assistant Examiner* — Oyeleye Alexander Alabi
(74) *Attorney, Agent, or Firm* — Occhiuti & Rohlicek LLP

(57) ABSTRACT

A wearable sensor for monitoring an external bodily fluid includes a sensor thread, a wick, a substrate, and a communication interface all of which are disposed on a substrate. The wick wicks the external bodily fluid to a functionalized region of the thread. The communication interface transmits, to an external device, data indicative of what the sensor thread has measured in said external bodily fluid. The external device can then carry out real-time analysis or storage.

23 Claims, 4 Drawing Sheets

(51) Int. Cl.

| | |
|---|---|
| A61B 5/145 | (2006.01) |
| A61B 5/1477 | (2006.01) |
| A61L 27/16 | (2006.01) |
| A61L 27/56 | (2006.01) |
| B01F 23/00 | (2022.01) |
| B01F 23/41 | (2022.01) |
| B01F 101/23 | (2022.01) |
| B01L 7/00 | (2006.01) |
| B01L 9/00 | (2006.01) |
| B23Q 17/24 | (2006.01) |
| C07K 14/705 | (2006.01) |
| C08F 220/56 | (2006.01) |
| C08L 33/26 | (2006.01) |
| C12M 1/34 | (2006.01) |
| C12Q 1/04 | (2006.01) |
| C12Q 1/18 | (2006.01) |
| C12Q 1/6844 | (2018.01) |
| C12Q 1/686 | (2018.01) |
| G01N 1/31 | (2006.01) |
| G01N 21/17 | (2006.01) |
| G01N 21/3577 | (2014.01) |
| G01N 21/359 | (2014.01) |
| G01N 21/39 | (2006.01) |
| G01N 21/45 | (2006.01) |
| G01N 21/64 | (2006.01) |
| G01N 21/77 | (2006.01) |
| G01N 21/78 | (2006.01) |
| G01N 27/414 | (2006.01) |
| G01N 30/12 | (2006.01) |
| G01N 30/68 | (2006.01) |
| G01N 30/70 | (2006.01) |
| G01N 30/72 | (2006.01) |
| G01N 30/88 | (2006.01) |
| G01N 33/00 | (2006.01) |
| G01N 33/18 | (2006.01) |
| G01N 33/50 | (2006.01) |
| G01N 33/53 | (2006.01) |
| G01N 33/543 | (2006.01) |
| G01N 33/68 | (2006.01) |
| G01N 33/74 | (2006.01) |
| G01N 35/00 | (2006.01) |
| G01N 35/04 | (2006.01) |
| G01N 35/10 | (2006.01) |
| G06F 1/16 | (2006.01) |
| G06T 7/00 | (2017.01) |
| G06T 7/90 | (2017.01) |
| G16H 20/60 | (2018.01) |
| G16H 40/63 | (2018.01) |
| H10K 10/46 | (2023.01) |
| H10K 85/00 | (2023.01) |
| H10K 85/20 | (2023.01) |

(56) References Cited

U.S. PATENT DOCUMENTS

| | | | |
|---|---|---|---|
| 2016/0310049 A1* | 10/2016 | Rowe | A61B 5/14517 |
| 2017/0231571 A1* | 8/2017 | Rogers | A61B 5/4266 |
| | | | 600/301 |
| 2018/0228436 A1 | 8/2018 | Sonkusale et al. | |
| 2020/0355617 A1 | 11/2020 | Sonkusale et al. | |

FOREIGN PATENT DOCUMENTS

| | | | | |
|---|---|---|---|---|
| WO | WO-2017023727 A1 * | 2/2017 | | A61B 5/00 |
| WO | 2017/189966 A1 | 11/2017 | | |
| WO | WO-2018125739 A1 * | 7/2018 | | A61B 5/14532 |
| WO | 2021030346 A1 | 2/2021 | | |

OTHER PUBLICATIONS https://www.netsys-direct.com/blogs/ethernetextender/what-is-twisted-pair-cable (Thompson _What is Twisted Pair Cable?) (Year: 2017).*

Mostafalu, Pooria, et al. "A toolkit of thread-based microfluidics, sensors, and electronics for 3D tissue embedding for medical diagnostics." Microsystems & Nanoengineering 2.1 (2016): 1-10. (Year: 2016).*

Kiyuan Liu et al. "Embroidered Electrochemical Sensors for Biomolecular Detection", Lab on a Chip, vol. 16, No. 11, Jan. 2016, pp. 2093-2097.

Pooria Mostafalu et al. "A toolkit of thread-based microfluidics, sensors and electronics for 3D tissue embedding for medical diagnostics", Microsystems & Nanoengineering, vol. 2, No. 1, Jul. 2016, pp. 2, 6-8.

International Search Report and Written Opinion, PCT Application No. PCT/US2019/051636, mailed May 13, 2020 (11 pages).

* cited by examiner

| Target Marker | Approach | Coating material for threads |
|---|---|---|
| pH | Potentiometric | 2 threads: carbon/PANI (WE), PVB/Ag/AgCl (RE) |
| glucose | Enzymatic - Amperometric | 3 threads: carbon/GOx (WE), PVB/Ag/AgCl (RE), carbon(CE) |
| lactate | Enzymatic- amperometric | 3 threads: carbon/LOx (WE), PVB/Ag/AgCl (RE), carbon(CE) |
| ethanol | Enzymatic- amperometric | 3 threads: carbon/AOx (WE), PVB/Ag/AgCl (RE), carbon(CE) |
| $pO_2$ | Galvanic | 2 threads: Zn (anode) and Ag (cathode) |
| $NH_4^+$ | Potentiometric | 2 thread: carbon/ $NH_4^+$ selective nonactin based membrane solution, PVB/Ag/AgCl (RE) |
| $Na^+$ | Potentiometric | 2 threads: carbon/$Na^+$ selective solution (WE), PVB/Ag/AgCl (RE) |
| $K^+$ | Potentiometric | 2 threads: carbon/$K^+$ selective solution (WE), PVB/Ag/AgCl (RE) |
| $Ca^{2+}$ | Potentiometric | 2 threads: carbon/$Ca^{2+}$ selective solution (WE), PVB/Ag/AgCl (RE) |
| Zn or Cd or Pb or Hg or As | Stripping voltammetric | 3 threads: carbon + Bi/Nafion(WE), PVB/Ag/AgCl (RE), carbon(CE) |
| cortisol | Amperometric/ Impedance | 3 threads: carbon+cortisol antibody/aptamer(WE), PVB/Ag/AgCl (RE), carbon(CE) |
| Cytokines (IL-1α,IL-, 1β,IL-6,TNF-α,IL-8, TGF-β, Neuropeptide NPY) | Amperometric/ Impedance | 3 threads: Carbon+ Analyte specific antibody/aptamer (WE), PVB/Ag/AgCl (RE), Carbon(CE) |

Table 1: Chemical Sensors on threads
WE: Working Electrode, RE: Reference Electrode, CE: Counter Electrode, GOx: Glucose Oxidase, LOx: Lactate oxidase, AOX: Alcohol oxidase, PANI: polyaniline, PVB: Polyvinyl Butyral

FIG. 3

THREAD-BASED REAL-TIME MONITORING OF BODILY FLUIDS

CROSS-REFERENCE TO RELATED APPLICATIONS

This application is a 371-application of International Application No. PCT/US2019/051636, filed Sep. 18, 2019, which claims the benefits of the filing date of U.S. Provisional Application No. 62/732,627, which was filed on Sep. 18, 2018, the contents of which are hereby incorporated by reference in their entirety.

STATEMENT OF GOVERNMENT RIGHTS

This invention was made with government support under contract W911QY-15-2-0001 awarded by the United States Army. The government has certain rights in the invention.

FIELD OF INVENTION

The invention relates to sensors, and in particular, to wearable sensors.

BACKGROUND

In order to monitor the condition of the human body, it is desirable to know what is inside the body. In particular, it is desirable to know what substances are being formed and in what amounts.

A difficulty that arises is that of entering the human body to learn this information. This requires making a hole. This both inflicts pain and provides a gateway for infection.

However, certain extruded bodily fluids also have biomarkers that can be used to assess the condition of the human body. Since these are extruded, they are available for sampling and analysis. For example, sweat glands produce copious quantities of sweat, each drop of which is brimming with biomarkers of interest. Other extruded fluids likewise carry biomarkers, all of which can be gathered non-invasively.

SUMMARY

The invention provides a wearable sensor-platform for real-time multiplexed monitoring of biomarkers in bodily fluids, and in particular, excreted bodily fluids that are easily available for analysis. Examples include sweat, tears, and urine. Being wearable, the sensor platform is by definition non-invasive. For example, in some embodiments, the sensor platform takes the form of a patch, and is therefore as non-invasive as an adhesive bandage.

In one aspect, the invention features a wearable sensor for monitoring one or more external bodily fluids, the wearable sensor comprising a substrate and various structures disposed on the substrate. These include a sensor thread, a wick, a substrate, and a communication interface. The wick wicks the external bodily fluid to a functionalized region on the sensor thread. The communication interface transmits data indicative of what the sensor thread has measured in the external bodily fluid.

In some embodiments, the substrate includes an adhesive bandage. However, the substrate can include any worn article that is routinely in contact with the skin, such as ornaments, including jewelry, clothing, wearable electronics, and certain fashion accessories.

In some embodiments, the wick comprises a gauze pad in contact with the thread. In others, the sensor threads comprise the wick.

Also among the embodiments are those in which the threads comprise reference threads and sensor threads as well as those in which the threads comprise threads coated with conductive carbon-ink and threads coated with Ag—AgCl ink.

In some embodiments, two of the threads define a portion of an electrochemical sensor.

Embodiments also include those in which threads are functionalized to detect cationic and anionic electrolytes, those in which the threads comprise a thread coated in an ion-selective membrane, and those in which comprise a thread functionalized with an enzyme. Examples of such electrolytes include ammonium, sodium, potassium, and hydrogen ions.

In yet other embodiments, the communication interface comprises an actuator.

These and other features of the invention will be apparent from the following detailed description and the accompanying figures, in which:

BRIEF DESCRIPTION OF THE DRAWINGS

FIG. 3 is a table summarizing the procedures for functionalizing threads for several representative applications.

DETAILED DESCRIPTION

Figure 1:
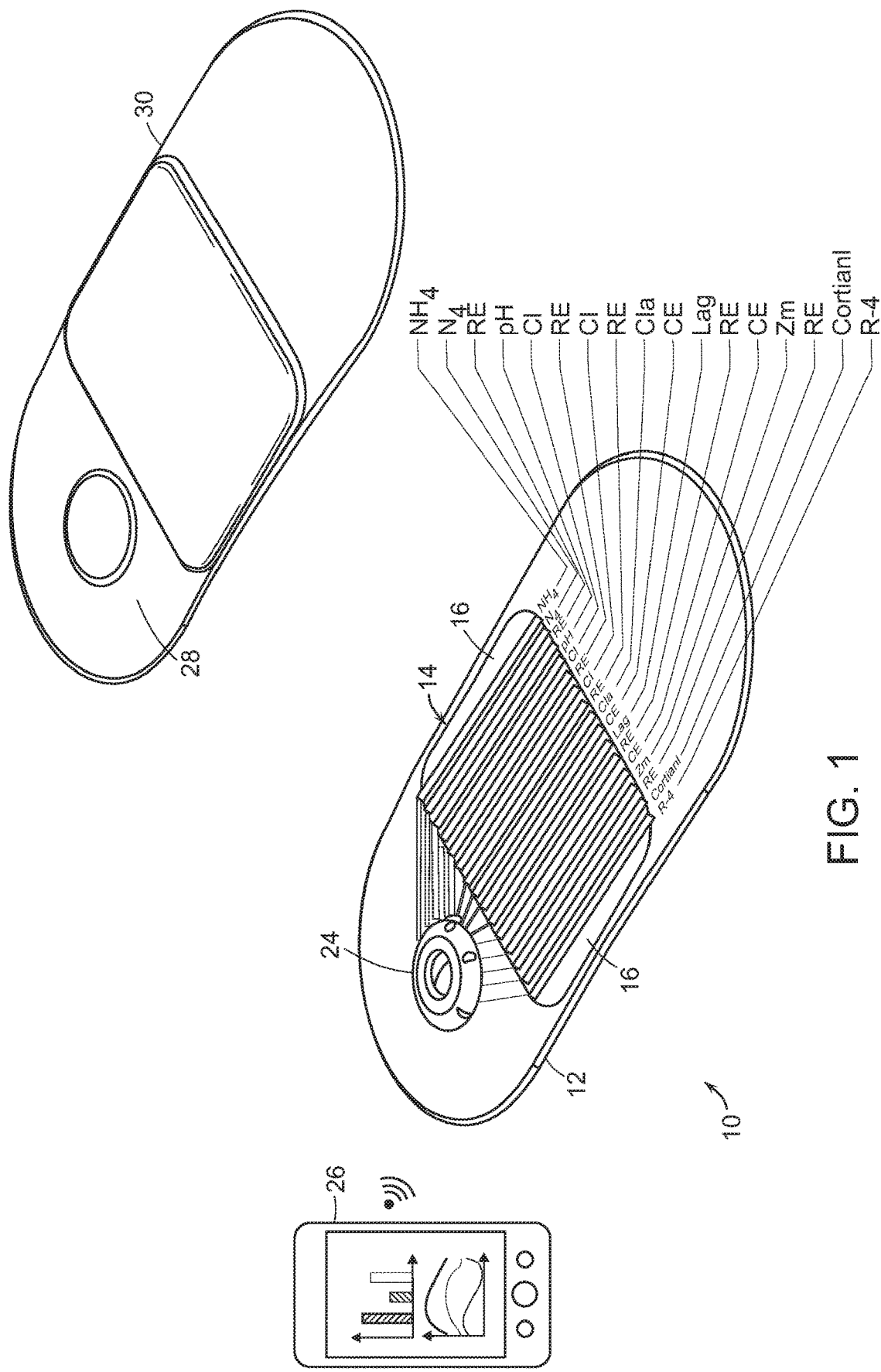
FIG. 1 shows a wearable sensor.

FIG. 1 shows a thread-based wearable sensor 10 having a substrate 12 on which is disposed a wick 14. Sensing threads 16 extend across the wick 14. The sensing threads 16 have been functionalized with appropriate sensor chemistry. Examples of suitable sensing threads 16 include those that are made of multi-filament polyester and those that are made of stainless steel.

Some of these threads 16 are measurement threads. Others are reference threads. A measurement thread is formed by coating a thread 16 with conductive carbon-ink. A reference thread is formed by coating a thread 16 with Ag—AgCl ink. For example, to form an electrochemical sensor, the working electrode is a measurement thread and the reference electrode is a reference thread.

The illustrated wearable sensor 10 provides continuous monitoring of any of a variety of bodily fluids, with the nature of the fluid being based primarily on the way the thread 16 is functionalized. Each thread 16 can be functionalized in a different way.

Examples of bodily fluids include sweat, urine, and tears. Certain key biomarkers are released into these fluids, thus making them useful for monitoring psychophysiological stress, inflammation, or chronic health conditions. Examples of biomarkers that are excreted with sweat include levels of electrolytes, such as sodium and ammonium ions, levels of metabolites, such as lactate, and acidity levels.

The particular biomarker sensed by a thread 16 depends on its manner of functionalization. It is possible, using appropriate functionalization, to cause a thread to detect cationic and anionic electrolytes, thus providing a way to measure pH, to detect metabolites and to detect heavy metals.

Some embodiments include a thread 16 that selectively carries out potentiometric sensing on particular species. Such threads can be made by coating a carbon thread with an ion-selective membrane or a pH sensitive material.

In other embodiments, a thread 16 detects metabolites. One way to functionalize a thread to carry this out is to immobilize metabolite-specific enzymes onto a carbon thread for amperometric detection. The immunoaffinity based electrical or electrochemical detection platform is developed using threads for detection of stress and inflammatory biomarkers. Detection of heavy metal/trace elements through electrochemical stripping using voltammetry is also carried out using threads 16.

Figure 2:
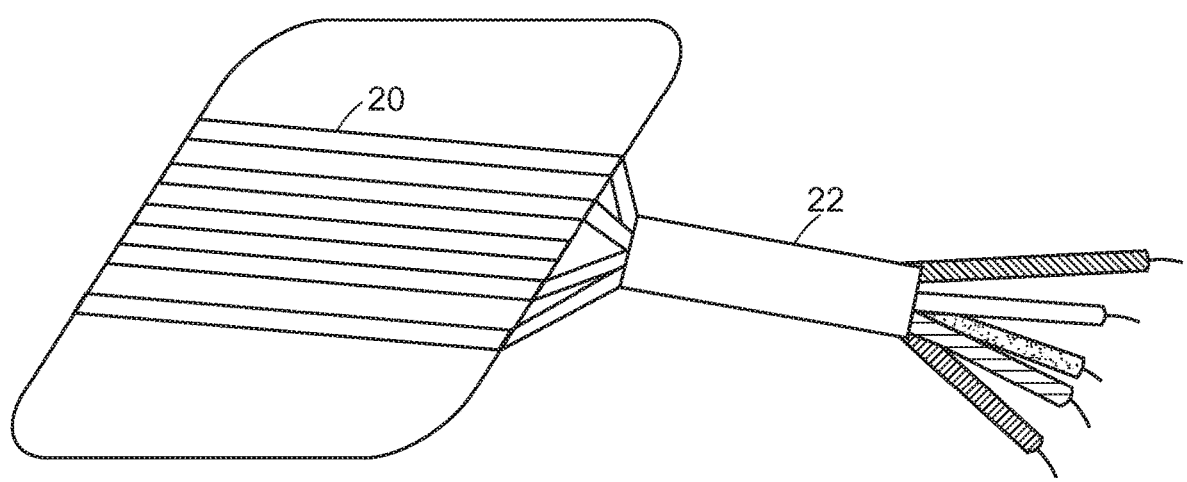
FIG. 2 shows a connector for the wearable sensor in FIG. 1.

Referring to FIG. 2, each thread 16 has a proximal end 18 that connects to a corresponding wire 20 in a bundle of wires 22. The wires 22 ultimately connect to a communication interface 24, which can be seen in FIG. 1. The communication interface 24 permits communication of data indicative of measurements to an external device 26 either for storage or so that real-time data analysis can be carried out. In some embodiments, an actuator button 28 on a cover 30 triggers such communication or turns the sensor 10 on and off.

The sensor 10 simultaneously and selectively detects multiple analytes such as electrolytes, ammonium, sodium, potassium, chloride etc., metabolites such as glucose, lactate, ethanol etc., as well as stress biomarkers such as cortisol, inflammation-related biomarkers such as cytokines and neuropeptides, heavy metals such as zinc, arsenic, lead, and mercury etc. FIG. 3 summarizes a few of the many functionalization methods and the target or marker that can be detected with such methods.

The illustrated substrate 12 on which the threads 16 are integrated is a flexible substrate 12 such as a dermal patch or an adhesive bandage. A particular dermal patch that is one sold under the trade name "TEGADERM™."

Figure 4:
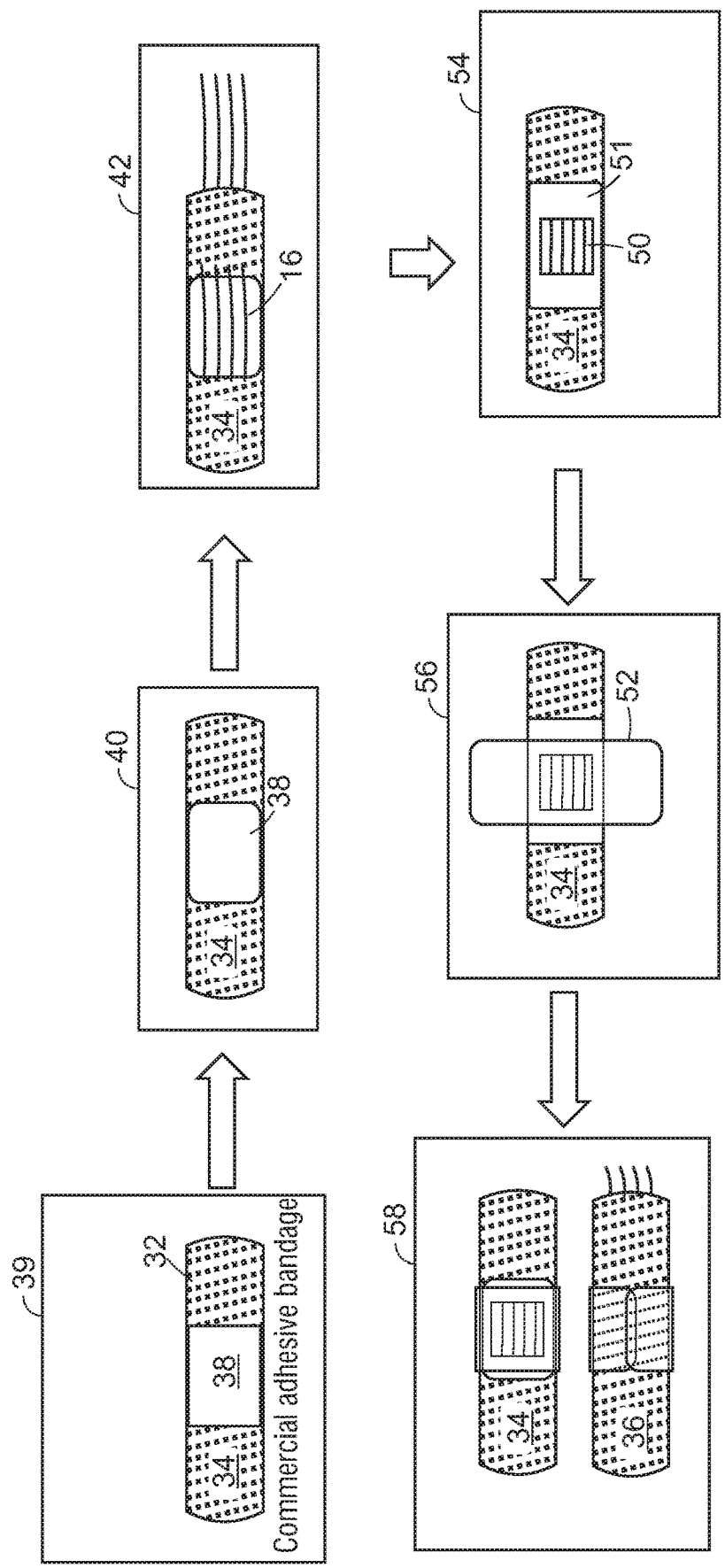
FIG. 4 shows steps in modifying a commercially-available adhesive bandage into a wearable sensor of the type described in connection with FIG. 1

Referring now to FIG. 4, a particularly simple way to make a wearable sensor is to start with a commercially-available adhesive bandage 32 (step 39). A commercially available bandage includes an inner face 34 that faces the skin and an outer face 36 that faces away from the skin. The inner face 34 typically has a rectangular piece of gauze attached to it. This will be referred to herein as the "first gauze 38."

The process for preparing a patch using an adhesive bandage 32 includes placing an adhesive hydrophobic film on the first gauze (step 40) and then placing the various threads 16 on this film (step 42). These would include a working thread, a reference thread, and a counter thread. The threads 16 can be sewn on or secured with tape. A suitable tape for this purpose is one based on a polyimide film such as poly (4,4'-oxydiphenylene-pyromellitimide).

A sensor area 50 is then defined by coating the threads 16 with dielectric ink and using a pattern to place insulating adhesive film 51 on the thread (step 54). The ends of the threads 16 are then coated with a conductive ink, such as silver ink, to promote electrical contact.

A difficulty that can arise in the configuration thus far is that once the threads 16 become soaked with sweat, they will be unable to take up newly-excreted sweat. Therefore, the measurement will become static.

To avoid this, it is useful to provide a second gauze 52 to implement an evaporation engine. The second gauze 52 is a patterned gauze that is placed over the threads 16 (step 56). This forms a sandwich in which the threads 16 lie between the first and second gauze 38, 52.

The second gauze 38 is made long enough so that it can be looped around the bandage 32 and thus cover the outer face 36 of the bandage (step 58).

The portion of the second gauze 52 over the outer face 36 is fully exposed to air. This promotes continuous evaporation and continuous wicking of sweat away from the threads 16. As a result, the threads 16 are able to take up freshly excreted sweat. This enables real-time sweat monitoring with a sample rate that depends on how fast sweat can be made to evaporate from the second gauze 52.

It is also possible to interweave or braid the threads 16 in association with other substrates 12 that permit skin contact. Suitable substrates include wearable electronic devices, such as wrist watches and headphones. Also suitable are wearable ornaments, such as jewelry, including bracelets, anklets, rings, and choker necklaces.

The threads 16 can also be woven into those parts of an article of clothing that would normally be in direct contact with the skin, such as the inner band of a shirt collar or socks. The threads 16 can also be incorporated into other wearable articles such as waistbands, headbands, hairbands, and either the temples, temple tips, or nose pads of either a pair of eyeglasses or a pair of goggles.

In the embodiment shown in FIG. 1, the substrate 12 is an adhesive bandage. In this embodiment, DuPont female connectors and housings connect the threads to a board having electronics for reading a voltage provided by the thread and communicating a signal representative of that voltage to an external device. In another embodiment, the threads 16 act as interconnects directly and do not require any female connector.

Further embodiments include individual interconnect threads that originate from individual the sensing threads and that are then braided or intertwined to form a multi-conductor thread cable.

The wick 14 in the embodiment shown in FIG. 1 is an absorbent gauze pad placed on top of the threads 16. The use of a wick 14 ensures the availability of a sufficient volume of sweat or body fluid.

In some cases, the sensor thread 16 itself wicks. This allows it to be exploited to carry bodily fluid from where it originates, through microfluidic channels, and onto a functionalized portion of the sensor thread 16.

Continuous wicking and evaporation or collection of the bodily fluid away from the functionalized portion of the sensor thread is achieved by a wicking medium, such as cloth, fabric, or gauze. Such removal of bodily fluid can also be achieved by exposing an end to the air to promote evaporation or by using a hydrophobic membrane covered superabsorbent polymer, such as sodium polyacrylate, derivatives thereof, or similar absorbent polymers that absorb liquid and turn into a gel.

The sensing threads are prepared using commercial threads such as polyester, stainless steel, cotton, nylon, silk, polyurethane, metallic threads, or threads that have been spun directly from conductive nanomaterials, such as graphene, reduced graphene oxide, or carbon nanotubes.

The threads coated with conductive carbon and silver/silver chloride ink using a reel-to-reel method and are used as working and reference thread electrode respectively.

One way to construct a potentiometric sensing thread is to coat a conductive working thread with an ion-selective polymeric membrane, for example by dipping it into a suitable solution. Another method that is useful for pH sensing threads is to carry out electrodeposition of polyaniline onto the thread.

Sensor threads that rely on enzyme immobilization, trapping, or encapsulation do so using a natural polymer matrix, such as chitosan or agarose, or similar biopolymers.

A sensor thread that relies on amperometric sensing of metabolites can be made by starting with a thread coated with a carbon-mediated ink and functionalizing it with covalent or electrostatic groups with or without linkers. A suitable carbon-mediated ink contains redox mediators based on ferrocene, ferrocyanide, ruthenium, or osmium.

It is also possible to functionalize a sensor thread using antibodies or aptamers. Such threads are further used in immunoaffinity based electrical or electrochemical sensing of biomarkers such as cortisol or cytokines.

In some embodiments, preparing a thread 16 begins by cleaning and air-drying the thread. In the case of a polyester thread, such cleaning can be carried out by soaking the thread in isopropanol.

Many commercially available threads have a wax coating that would inhibit the thread's ability to be infused with conductive ink. To accommodate this difficulty, some practices of the preparation method include an optional step of removing this wax. A suitable method for doing so is to expose the thread to air plasma for a limited period, for example, on the order of five minutes.

With the polyester thread having been rendered more hydrophilic, the next step is that of infusing it with a suitable conductive liquid. In some practices, this includes infusing the thread in an ink that comprises silver and silver chloride and then curing it in a 60° C. oven for half an hour. Such a thread is useful as a reference electrode. Other practices include infusing the thread with a carbon-containing resistive ink. This results in a carbon/polyester electrode and carrying out a similar curing procedure.

Preparation of stainless-steel thread includes cleaning the thread with isopropyl alcohol, coating it with carbon resistive ink, and then baking it in a 60° C. oven for about thirty minutes. Such a thread is particularly useful as a pH sensor.

Functionalizing a thread to sense an electrolyte includes coating the thread with a suitable solution that forms an ion-selective membrane that passes only the electrolyte of interest.

A solution for forming an ammonium-selective membrane is prepared by dissolving 0.4 milligrams of nonactin, 138 milligrams of o-NPOE and 61.6 milligrams of PVC in 2 milliliters of THF and mixing for thirty minutes in an ultrasonic bath. To complete the functionalization process, a polyester thread that has been coated in carbon-based resistive ink is then dip-coated with the above solution to coat it on a layer-by-layer basis. A suitable number of layers is four. The thread is then allowed to dry.

A solution for forming a sodium-selective membrane is prepared by dissolving 2 milligrams of selectophore grade sodium ionophore X, Na-TFPB, 66 milligrams of PVC and 130.9 mg of DOS dissolved in 1.32 milliliters of THF and mixing for thirty minutes in an ultrasonic bath. To complete the functionalization process, a polyester thread that has been coated in carbon-based resistive ink is then dip-coated with the above solution to form a suitable coating on a layer-by-layer basis. A suitable number of layers is three. The thread is then allowed to dry.

A solution for forming a hydrogen-selective membrane is prepared by dissolving 500 milligrams of PANI base in 100 milliliters of hydrochloric acid (HCl) placed in a ~4° C. ice bath for five hours. The thread is then subjected to electrochemical deposition of polyaniline on its surface. A suitable procedure is to immerse the thread in aniline solution and expose it to seventy seconds of a 150 microamp anodic current. Prior to using the thread, it is preferable to wash the resulting functionalized thread several times in deionized water to remove any aniline residues from its surface.

A solution for a reference electrode is prepared by dissolving 78 1 milligrams of PVB and 50 milligrams of sodium chloride into 1 milliliter of methanol and mixing for about thirty minutes in an ultrasonic bath. The electrode is then prepared by starting with a polyester thread having a coating of silver chloride and a coating of silver, dipping that thread in the PVB solution, and allowing the thread to dry for an hour.

In some cases, it is of interest to sense levels of lactate in sweat. This requires functionalizing a thread so that it detects lactate. To carry out this procedure, one begins with a polyester thread, coats it with Prussian-blue mediated ink, and cures it in a 60° C. oven for thirty minutes. This results in a PB-coated thread. The next step is to define an active surface area on the thread. This can be carried out by coating the thread with a dielectric ink.

The next step includes preparing a solution of chitosan (1% w/v) in 0.1 M acetic acid by magnetic stirring for an hour at room temperature. The chitosan solution is then mixed with an equal amount of PBKCl. The resulting diluted chitosan solution is drop cast onto the PB-coated threads. The thread is then dried and later coated with lactate oxidase and chitosan solution. Such threads should be stored at a cool temperature, for example at around 4° C.

Having described the invention and a preferred embodiment thereof, what is claimed as new and secured by Letters Patent is:

1. An apparatus comprising a wearable sensor configured for real-time multiplexed monitoring of biomarkers in an external bodily fluid, said wearable sensor comprising a substrate, a communication interface disposed on said substrate, a wick disposed on said substrate, and a thread disposed on said wick, said thread being a sensor thread that has a functionalized region, wherein said wick wicks said external bodily fluid to said functionalized region, wherein said communication interface transmits data indicative of what said sensor thread has measured in said external bodily fluid, wherein said thread is one of a plurality of threads, each of which comprises a proximal end that connects to a corresponding wire in a bundle of wires, wherein each of said wires in said bundle of wires connects to said communication interface, and wherein said communication interface communicates data indicative of measurements obtained by each of said threads for storage or real-time data analysis, wherein said thread is disposed on a substrate selected from the group consisting of a bandage and a dermal patch, said substrate having an outer face.

2. The apparatus of claim 1, wherein said wick comprises a gauze pad in contact with said thread.

3. The apparatus of claim 1, wherein said thread is one of a plurality of sensor threads that comprise said wick.

4. The apparatus of claim 1, wherein said plurality of threads comprises threads that have been functionalized for detection of electrolytes, threads that have been functionalized for detection of metabolites, threads that have been functionalized to detect stress biomarkers, and threads that have been functionalized to detect inflammation-related biomarkers.

5. The apparatus of claim 1, wherein said plurality of threads comprise a first, second, and third thread that implement a working electrode, a reference electrode, and a counter-electrode, respectively, wherein said first, second, and third threads cooperate to sense presence of a heavy metal.

6. The apparatus of claim 1, wherein said thread is functionalized to detect cationic and anionic electrolytes.

7. The apparatus of claim 1, wherein said real-time multiplexed monitoring is carried out with a sample rate that depends on how fast said external bodily fluid evaporates.

8. The apparatus of claim 1, wherein said plurality of threads comprises first, second, and third thread that implement a working electrode, a reference electrode, and a counter-electrode, respectively, wherein said first, second, and third threads cooperate to sense presence of cytokines.

9. The apparatus of claim 1, further comprising a cover, wherein said communication interface comprises an actuator that triggers communication by said communication interface or turns said sensor on and off.

10. The apparatus of claim 1, wherein said plurality of threads implements sensors for detecting said biomarkers in said external bodily fluid, wherein at least some of said sensors comprise three of said threads and at least some of said sensors comprise two of said threads.

11. The apparatus of claim 1, wherein said threads comprise interconnects for interconnecting with said communication interface.

12. The apparatus of claim 1, further comprising an evaporation engine that promotes continuous take up of said external bodily fluid.

13. The apparatus of claim 1, further comprising first and second gauze, wherein said thread is disposed between said first gauze and said second gauze, and wherein said second gauze is a patterned gauze.

14. The apparatus of claim 1, wherein said thread is functionalized for detection of lactate in sweat.

15. The apparatus of claim 1, wherein said thread is coated with Prussian blue.

16. The apparatus of claim 1, wherein said thread comprises chitosan.

17. The apparatus of claim 1, further comprising a gauze that covers said outer face of said substrate.

18. The apparatus of claim 1, wherein said substrate comprises said bandage.

19. The apparatus of claim 1, wherein said substrate comprises said dermal patch.

20. The apparatus of claim 1, further comprising a gauze, wherein said substrate comprises said bandage and said gauze is long enough to loop around said bandage and to cover said outer face of said substrate.

21. The apparatus of claim 18, wherein said bandage is an adhesive bandage.

22. The apparatus of claim 21, wherein said communication interface comprises a board having electronics for reading voltages provided by said threads and communicating a signal representative of said voltages to an external device.

23. The apparatus of claim 1, wherein said wires in said bundle of wires extend from said wick and across said substrate to connect proximal ends of said sensor threads to said communication interface.

* * * * *